United States Patent
Majima et al.

(10) Patent No.: US 10,208,094 B2
(45) Date of Patent: Feb. 19, 2019

(54) MULTIMERIC IMMUNOGLOBULIN-BINDING DOMAIN

(71) Applicant: PROTENOVA CO., LTD., Higashikagawa-shi, Kagawa (JP)

(72) Inventors: Eiji Majima, Naruto (JP); Atsushi Shima, Itano-gun (JP)

(73) Assignee: PROTENOVA CO., LTD., Naruto-shi (JP)

(*) Notice: Subject to any disclaimer, the term of this patent is extended or adjusted under 35 U.S.C. 154(b) by 344 days.

(21) Appl. No.: 14/916,316

(22) PCT Filed: Sep. 4, 2014

(86) PCT No.: PCT/JP2014/073325
§ 371 (c)(1),
(2) Date: Mar. 3, 2016

(87) PCT Pub. No.: WO2015/034000
PCT Pub. Date: Mar. 12, 2015

(65) Prior Publication Data
US 2016/0215027 A1 Jul. 28, 2016

(30) Foreign Application Priority Data
Sep. 4, 2013 (JP) ................. 2013-183333

(51) Int. Cl.
C07K 14/31 (2006.01)
C07K 1/22 (2006.01)
C07K 16/12 (2006.01)

(52) U.S. Cl.
CPC ............... *C07K 14/31* (2013.01); *C07K 1/22* (2013.01); *C07K 16/1271* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 5,580,788 A * | 12/1996 | Kihira | C07K 14/31 435/69.1 |
| 6,399,750 B1 | 6/2002 | Johansson | |
| 2005/0143566 A1 | 6/2005 | Hober | |
| 2006/0194950 A1 | 8/2006 | Hober et al. | |
| 2006/0194955 A1 | 8/2006 | Hober et al. | |
| 2008/0051555 A1 | 2/2008 | Iwakura et al. | |
| 2009/0299035 A1 | 12/2009 | Iwakura et al. | |
| 2010/0022760 A1 | 1/2010 | Hober et al. | |
| 2010/0130721 A1 | 5/2010 | Iwakura et al. | |
| 2010/0286373 A1 | 11/2010 | Majima et al. | |
| 2011/0112276 A1 | 5/2011 | Hober | |
| 2012/0238724 A1 | 9/2012 | Hober | |
| 2013/0184438 A1 | 7/2013 | Hober et al. | |
| 2014/0107315 A1 | 4/2014 | Yoshida et al. | |

FOREIGN PATENT DOCUMENTS

| | | | |
|---|---|---|---|
| JP | 2005-112827 A | 4/2005 | |
| JP | 4117903 B2 | 5/2008 | |
| JP | 4179517 B2 | 9/2008 | |
| JP | 2008-266219 A | 11/2008 | |
| JP | 2008-266221 A | 11/2008 | |
| JP | 4391830 B2 | 10/2009 | |
| JP | 5004165 B2 | 6/2012 | |
| WO | WO-2007019376 A2 * | 2/2007 | ........... A61K 49/085 |
| WO | WO-2008039141 A1 * | 4/2008 | ......... B01D 15/3809 |
| WO | 2012/133349 A1 | 10/2012 | |

OTHER PUBLICATIONS

Ljungquist, et al., "Thiol-directed immobilization of recombinant IgG-binding receptors", Eur. J. Biochem., 186, (1989), pp. 557-561.
Saito, et al., "High level expression of a synthetic gene coding for IgG-binding domain B of *Staphylococcal* Protein A", Protein Engineering, vol. 2, No. 6, 1989, pp. 481-487.
Nilsson, et al., "A synthetic IgG-binding domain based on *Staphylococcal* protein A", Protein Engineering, vol. 1, No. 2, 1987, pp. 107-113.
Von Roman, et al., "Improving the binding capacities of protein A chromatographic materials by means of ligand polymerization", Journal of Chromatography A, 1347, (2014), pp. 80-86.
International Search Report dated Dec. 9, 2014, issued in counterpart International Application No. PCT/JP2014/073325. (2 pages).

* cited by examiner

*Primary Examiner* — Daniel E Kolker
*Assistant Examiner* — James L Rogers
(74) *Attorney, Agent, or Firm* — Westerman, Hattori, Daniels & Adrian, LLP (57) ABSTRACT

A multimeric immunoglobulin-binding protein having improved properties as an affinity ligand for affinity chromatography, and an insoluble support immobilizing such a multimer. The immunoglobulin-binding protein is represented by the formula: $(R1)_n\text{-}(R2)_m$, or $(R2)_m\text{-}(R1)_n$. R2 is an immunoglobulin-binding domain including an amino acid residue that covalently bonds to an insoluble support upon immobilization reaction with the insoluble support, and R1 is an immunoglobulin-binding domain without containing an amino acid residue the presence of which in the sequence compared to when it is absent in the sequence reduces the immunoglobulin-binding activity of the support yielded by the immobilization reaction. The immunoglobulin-binding protein satisfies: (1) n is an integer of 5 to 9; (2) m is an integer of 1 or 2; (3) the n (R1) domains may or may not have the same sequence; and (4) the total number of domains (n+m) is 6 to 10.

9 Claims, 3 Drawing Sheets
Specification includes a Sequence Listing.

MULTIMERIC IMMUNOGLOBULIN-BINDING DOMAIN

TECHNICAL FIELD

The present invention relates to a protein having affinity to immunoglobulins, an insoluble support immobilizing the protein, and a method for separating and purifying an immunoglobulin using the insoluble support. Specifically, the invention relates to a multimeric immunoglobulin-binding protein having improved properties as an affinity ligand for affinity chromatography, or, to be more specific, a multimer of linked immunoglobulin-binding domains. The present invention also relates to an immobilization support for oriented immobilization of a multimeric immunoglobulin-binding protein, and to affinity separation of immunoglobulins.

BACKGROUND ART

The growing demand for antibodies accompanied by rapid development of antibody drugs has increased the demand for higher antibody purification efficiency and thus higher antibody binding capacity for an affinity gel support used for antibody purification with the immobilized immunoglobulin-binding protein. For immobilization of an immunoglobulin-binding protein on an insoluble support, reactivity of side chains of its amino acid residues are utilized. In order to increase the immunoglobulin binding amount, there have been various attempts to orientationally immobilize protein.

The present inventors have invented an immunoglobulin-binding protein with an orientationally controllable immunoglobulin-binding domain. Specifically, the present inventors selected a C domain with high alkali stability from the five immunoglobulin-binding domains of *Staphylococcus* protein A gene, and modified parts of its amino acid sequence to allow the protein to be disposed in such an orientation that the immunoglobulin binding site will not be blocked, and the binding of the protein to an immunoglobulin will not be inhibited when the protein is immobilized on a support via one or more lysine residues (PTL 1).

There is also an attempt to achieve oriented single-point immobilization by introducing cysteine to the C-terminus of a protein, and immobilizing the protein on a gel support via a disulfide bond (NPL 1) or a thioether bond (PTL 2). In another attempt, immobilization is controlled with the N-terminal α-amino group (PTL 3) or the C-terminal carboxyl group (PTL 5) of an immunoglobulin-binding protein that has had its lysine residues substituted with some other amino acid.

The previous report introducing a cysteine residue to C-terminus, and the report using a C-terminal carboxyl group or an N-terminal amino group for oriented, single-point immobilization achieve increased immunoglobulin G (IgG) binding amounts. However, it remains elusive as to the optimum number of monomers (domains) linked to construct an immunoglobulin-binding domain multimer. For example, NPL 1 produces a monomer, a dimer, and a pentamer that are immobilized on thiopropyl sepharose at one location via an S—S bond with the cysteine introduced to the C-terminus of a Z domain modified from the B domain of protein A. However, the support immobilizing the pentamer is described as yielding the same IgG binding amount as the dimer-immobilized support. NPL 2 produces a multimer of four linked B domains of protein A. However, it is reported that the tetramer had essentially the same activity as that of native-form protein A (SPA) of five binding domains, and was no different from the pentamer. This paper measures the precipitation levels of the complex formed, but does not evaluate the multimer with regard to immobilization on a gel support and its binding capacity. NPL 3 produces a monomer, a dimer, a pentamer, and a decamer of a Z domain. However, while these are shown to have IgG binding activity, the proteins are not immobilized on a gel support, or not measured for IgG binding on a support.

In PTL 4, the C-terminal carboxyl group is orientationally immobilized. This publication describes a dimer with two linked domains as having about the same level of binding strength as heteropentameric native-form protein A. PTL 2 successfully produces a support of high immunoglobulin binding capacity by introducing cysteine to the C-terminus of the amino acid sequence of pentameric native-form protein A, and orientationally immobilizing the protein via a thiol group. However, this publication does not give any consideration to multimers of order higher than pentamers. PTL 2 describes the pentamer as having an IgG molar binding ratio of 2 to 3. PTL 3 and PTL 5 describe repeating 2 to 5 binding domains, but do not clearly state the optimum number of repeats. PTL 6 in paragraph [0033] describes a tetramer as being most desirable among the dimeric to pentameric multimers of an alkali-stabilized Z-domain variant.

It has been previously reported that the number of repeating immunoglobulin-binding domains is desirably 2 to 5. However, there is no report that indicates the usefulness of multimers of more than five domains compared to native-form protein A having five domains. Specifically, it has been unclear as to the optimum number of binding domains that maximizes the immunoglobulin-binding activity when a multimer with more than one binding domain is immobilized on a support at the terminal portion, irrespective of the chemical reaction used to immobilize the protein.

CITATION LIST

PTL

PTL 1: Japanese Patent No. 4179517
PTL 2: Japanese Patent No. 4117903
PTL 3: JP-A-2008-266219
PTL 4: JP-A-2005-112827
PTL 5: Japanese Patent No. 5004165
PTL 6: Japanese Patent No. 4391830

Non PTL

NPL 1: Eur. J. Biochem. 1989 (186) 557-561
NPL 2: Protein Engineering 1989 (2) 481-487
NPL 3: Protein Engineering 1987 (1) 107-113

DISCLOSURE OF INVENTION

Technical Problem

Problems and Solutions

The present invention is the result of finding a solution the problems of the related art after finding a clue to the problems in the following thinking process. Specifically, it was contemplated that oriented immobilization of an immunoglobulin-binding protein would increase the amount of the immobilized protein, and that the IgG binding amount would increase in proportion to the number of IgG binding domains. It follows from this that the IgG binding amount would increase by increasing the immobilization amount of the multimeric immunoglobulin-binding protein having repeatedly linked binding domains. Because native protein A is a pentamer, previous studies have examined dimers to pentamers. However, there is no study that thoroughly examines the number of linked monomers and the amount of IgG binding it produces in orientationally immobilizing a multimer of order higher than pentamers. It would be possible to bind larger numbers of IgG if larger numbers of IgG binding domains could be orientationally immobilized. In practice, however, binding of IgG having a molecular weight of about 150,000 requires not only increasing the number of binding domains, but providing enough space between binding domains so that an IgG molecule that has attached to a binding domain does not interfere with access and binding of the nearby IgG molecules. Here, there should be the optimum immobilization amount of IgG binding domains that maximizes the IgG binding amount. In a multimer with linked IgG binding domains, there also should be the optimum length and the optimum immobilization amount that do not interfere with binding of IgG molecules.

It has been thought that the most desirable structure of an immunoglobulin-binding protein is where the protein has a repeat of at most four binding domains because the immunoglobulin binding amount of an immunoglobulin-binding protein immobilized on a support does not increase even when the protein has more than four binding domains. While the immunoglobulin binding amount of an immunoglobulin-binding protein immobilized on a support is proportional to the amount of the binding domains, the immunoglobulin binding amount is also greatly influenced by the support structure, including the pore size, the space volume, and the effective surface area. The effect of the support structure on immunoglobulin binding becomes more notable in multimers having a repeated structure of binding domains than small, folded spherical proteins because such multimers occupy a large volume. An orientationally immobilized multimer has a highly flexible structure with spatially stretched binding domains, and has more opportunities to contact the immunoglobulin. This enhances the binding capacity. However, because the binding property is affected by the pore size of the support, the number of multimer binding domains is not necessarily proportional to the immunoglobulin binding amount. As commonly experienced in using an affinity support, increasing the amount of immobilized multimer on a support often leads to reduced binding amounts because of the steric hinderance preventing binding of immunoglobulin molecules to the protein as the immunoglobulin molecules are brought close to each other in a space. Because of these factors affecting the binding capacity of an immunoglobulin-binding protein immobilizing support, it has remained unclear how the binding domain repeating structure of a multimer is related to immunoglobulin binding amounts.

An object of the present invention, directed to maximizing the immunoglobulin binding amount of an affinity gel support used for purification of immunoglobulin, is to optimize the binding domain repeating structure of a multimeric immunoglobulin-binding protein orientationally immobilized on a support, and find the optimum multimer structure that yields the maximum immunoglobulin binding amount with less immobilization amount.

Solution to Problem

In order to achieve the foregoing object, the present inventors produced various orientationally immobilizable multimeric immunoglobulin-binding proteins using genetic engineering techniques, and conducted detailed comparative studies of the protein purified from each transformant with regard to the immunoglobulin binding amount of the support immobilizing the protein. The present invention has thus been completed, as follows.

(1) An immunoglobulin-binding protein as a multimer of immunoglobulin-binding domains represented by the following general formula:

(R1)$n$-(R2)$m$, or (R2)$m$-(R1)$n$, wherein R2 is an immunoglobulin-binding domain occurring at the N-terminus or the C-terminus of the protein, and that includes an amino acid residue that covalently bonds to an insoluble support upon immobilization reaction with the insoluble support, and R1 is an immunoglobulin-binding domain that does not contain an amino acid residue the presence of which in the sequence compared to when it is absent in the sequence reduces the immunoglobulin-binding activity of the support yielded by the immobilization reaction, the immunoglobulin-binding domains comprising an amino acid sequence with the left end representing the N-terminus and the right end representing the C-terminus, the immunoglobulin-binding protein having properties that satisfy the following conditions, and that allow the immunoglobulin-binding protein to be immobilized on the insoluble support via the amino acid residue of the (R2) domain:

(1) n is an integer of 5 to 9;
(2) m is an integer of 1 or 2;
(3) the n (R1) domains may or may not have the same sequence; and
(4) the total number of domains (n+m) is 6 to 10.

(2) The immunoglobulin-binding protein according to (1), wherein the (R1) domain in the foregoing structural formula is an amino acid sequence in which a non-lysine amino acid has replaced the original lysine residues of the amino acid sequence only in lysine residues the presence of which in the sequence compared to when these are absent in the sequence reduces the immunoglobulin-binding activity of the support yielded by the immobilization reaction with the insoluble support, and wherein the (R2) domain is an amino acid sequence containing a lysine residue that covalently bonds to the insoluble support upon immobilization reaction.

(3) The immunoglobulin-binding protein according to (1) or (2), wherein the (R2) domain in the foregoing structural formula comprises:

an amino acid sequence sharing the same properties as the (R1) domain, and that does not contain an amino acid residue the presence of which in the sequence compared to when it is absent in the sequence reduces the immunoglobulin-binding activity of the support yielded by the immobilization reaction; and an amino acid sequence containing two or more lysine residues and added to the terminal not linked to the (R1) domain.

(4) The immunoglobulin-binding protein according to (1) or (2), wherein the (R2) domain in the foregoing structural formula comprises:

the amino acid sequence of the immunoglobulin-binding protein;

the amino acid sequence of the immunoglobulin-binding protein with the substitution of some of the lysine residues with amino acids other than lysine; or the amino acid sequence of the immunoglobulin-binding protein with the substitution of some of the lysine residues with amino acids other than lysine, and with the substitution of some of the non-lysine amino acid residues with lysine.

(5) The immunoglobulin-binding protein according to any one of (1) to (4), wherein the immunoglobulin-binding domains (R1) and (R2) of the structural formula each comprise a domain modified from the amino acid sequence of the immunoglobulin-binding domain of *Staphylococcus* protein A.

(6) The immunoglobulin-binding protein according to (5), wherein the (R2) domain in the structural formula comprises an immunoglobulin-binding domain based on the amino acid sequence of the immunoglobulin-binding domain of *Staphylococcus* protein A in which the lysine residues originally present in the sequence are substituted with a non-lysine amino acid only at position 35, or at position 35 and one or more positions in positions 4, 7, and 35 of the amino acid sequence.

(7) The immunoglobulin-binding protein according to (6), wherein the (R2) domain derived from the protein A includes substitution of 1 to 6 amino acid residues with lysine at positions 40, 43, 46, 53, 54, and 56 of the amino acid sequence.

(8) The immunoglobulin-binding protein according to any one of (5) to (7), wherein the (R1) domain of the structural formula comprises a sequence based on the amino acid sequence of the immunoglobulin-binding domain of *Staphylococcus* protein A in which the lysine residues originally present in the sequence are substituted with a non-lysine amino acid at 1 to 3 of positions 4, 7, and 35.

(9) The immunoglobulin-binding protein according to (8), wherein the (R1) domain of the structural formula comprises a sequence in which the original lysine residues are further substituted with a non-lysine amino acid at 1 to 4 of positions 42, 49, 50, and 58.

(10) An immunoglobulin-binding immobilization support comprising the immunoglobulin-binding protein of any one of (1) to (9) immobilized on an insoluble support.

(11) A method for separating and purifying an immunoglobulin with the immunoglobulin-binding immobilization support of (10).

Advantageous Effects of Invention

The present invention found the optimum multimer structure that yields the maximum immunoglobulin binding amount with small immobilization amounts for the oriented immobilization of a protein (e.g., a variant of protein A) of a multimeric structure containing linked immunoglobulin-binding protein monomers (domains) on an insoluble support. Modified immunoglobulin-binding proteins of the related art contain 2 to 5 linked binding domains, and are immobilized on a support in amounts large enough to enable immobilization but small enough to prevent inhibiting immunoglobulin activity. The present invention, by using a support immobilizing small amounts of immunoglobulin-binding protein, can achieve the maximum immunoglobulin binding with certain amounts of support, regardless of the immobilization reaction used to immobilize the protein on the support. The invention can thus contribute to reducing the cost of antibody production, and improving the efficiency of antibody production in areas using antibodies.

DESCRIPTION OF EMBODIMENTS

The present invention relates to an immunoglobulin-binding protein as a multimer of immunoglobulin-binding domains represented by the following general formula:

(R1)$n$-(R2)$m$, or (R2)$m$-(R1)$n$, wherein R2 is an immunoglobulin-binding domain occurring at the N-terminus or the C-terminus of the protein, and that includes an amino acid residue that covalently bonds to an insoluble support upon immobilization reaction with the insoluble support, and R1 is an immunoglobulin-binding domain that does not contain an amino acid residue the presence of which in the sequence compared to when it is absent in the sequence reduces the immunoglobulin-binding activity of the support yielded by the immobilization reaction, the immunoglobulin-binding domains comprising an amino acid sequence with the left end representing the N-terminus and the right end representing the C-terminus, the immunoglobulin-binding protein having properties that satisfy the following conditions, and that allow the immunoglobulin-binding protein to be immobilized on the insoluble support via the amino acid residue of the (R2) domain:

(1) n is an integer of 5 to 9;
(2) m is an integer of 1 or 2;
(3) the n (R1) domains may or may not have the same sequence; and
(4) the total number of domains (n+m) is 6 to 10.

The present invention also relates to an immunoglobulin-binding immobilization support linked to the protein, and to a method for separating and purifying an immunoglobulin with the support in affinity chromatography.

A multimer of the present invention is an immunoglobulin-binding protein having a total of 6 to 10 immunoglobulin-binding domains. The immunoglobulin-binding protein has a characteristic structure that the 1 to 2 terminal (R2) domains are immobilized on an insoluble support, whereas the 5 to 9 linked (R1) domains remain highly mobile on the insoluble support without being immobilized. Because only the (R2) domains are selectively immobilized on the support via a covalent bond, it is possible to achieve a highly selective immobilization reaction through a reaction that takes advantage of the high reactivity of amino acids such as a lysine residue, and a cysteine residue. The (R1) domain constructing the multimer has an amino acid sequence that does not contain an amino acid that is active to the chemical reaction used for immobilization, whereas the (R2) domain in the multimer has an amino acid sequence containing an amino acid that is active to the chemical reaction used for immobilization.

When the immobilization reaction used to immobilize the protein on the support takes place via an amino group, an (R2) domain capable of binding to an immunoglobulin and having enhanced immobilization reactivity can be produced by substituting the lysine residues contained in the amino acid sequence of an immunoglobulin-binding domain used for the (R2) domain with non-lysine amino acids only in lysine residues occurring at positions that interfere with binding to an immunoglobulin upon immobilizing the protein on the support, and by substituting some of the non-lysine amino acids not involved in binding to an immunoglobulin with lysine. The present invention becomes implementable when the (R1) domain linked to such an (R2) domain is an immunoglobulin-binding domain of the sequence in which a non-lysine amino acid has replaced the original lysine residues of the amino acid sequence only in lysine residues the presence of which in the sequence compared to when these are absent in the sequence reduces the immunoglobulin-binding activity of the support yielded by the immobilization reaction with the insoluble support.

When the (R2) domain is one in which some of the lysine residues originally present in the sequence have been substituted with non-lysine amino acids as in the (R1) domain, the multimer can be orientationally immobilized on the insoluble support via lysine residues when a peptide containing more than one lysine is added to the amino acid sequence terminal not attached to the (R1) domain.

In the case of an immobilization reaction via a thiol group, the present invention becomes implementable upon introducing a new cysteine residue to the immunoglobulin-binding domain used as (R2) domain. In this case, the sequence of the (R1) domain linked to the (R2) domain is cysteine free. A support immobilization reaction using a disulfide bond or a maleimide group that is highly selective to the thiol group may be used for immobilization of the cysteine-introduced multimer. An epoxy group commonly used in industry for its low cost and high chemical stability easily forms a thioether bond with cysteine, and can be used for immobilization of the cysteine-introduced multimer on a support.

Other methods are also available that use a cysteine residue for immobilization, including the method described in PTL 5 in which a thiol group is cyanylated to achieve immobilization on an amino group-containing immobilization support, and the method described in PTL 2 in which a multimer having a cysteine residue is immobilized on an amino group-containing support using 4-(N-maleimidomethyl)cyclohexane-1-carboxylate (SMCC) as a crosslinker.

To describe more specifically, the immunoglobulin-binding domain (R1) of the foregoing structural formula is preferably an amino acid sequence in which a non-lysine or non-cysteine amino acid has replaced the original lysine residues of the amino acid sequence only in lysine residues the presence of which in the sequence compared to when these are absent in the sequence reduces the immunoglobulin-binding activity of the support yielded by the immobilization reaction with the insoluble support, and the immobilization binding domain (R2) is preferably a domain with an amino acid sequence containing a lysine residue and/or a cysteine residue that covalently bonds to the support upon an immobilization reaction with the insoluble support. For example, the immunoglobulin-binding domains represented by (R1) and (R2) may each be a domain modified from the amino acid sequence of the binding domain of *Staphylococcus* protein A. In this case, the immunoglobulin-binding domain (R1) may contain a lysine residue, provided that the immunoglobulin-binding activity in the immobilization reaction does not differ when a lysine residue is present as in the original sequence and when a lysine residue is substituted.

The domain (R2) can have enhanced immobilization to the support when the immunoglobulin-binding domain (R1) is an immunoglobulin-binding domain based on the amino acid sequence of the immunoglobulin-binding domain of *Staphylococcus* protein A in which one or more of the lysines originally present therein are substituted with a non-lysine amino acid at positions 4, 7, and 35, or an immunoglobulin-binding domain in which 1 to 4 of the original lysine residues are additionally substituted with a non-lysine amino acid at positions 42, 49, 50, and 58 to reduce the number of lysine residues involved in immobilization of (R1).

The domain (R2) can have enhanced bondability to the support when (R2) is an immunoglobulin-binding domain based on the amino acid sequence of the immunoglobulin-binding domain of *Staphylococcus* protein A in which the lysine residues originally present in the sequence are substituted with a non-lysine amino acid only at position 35, or at position 35 and one or more positions in positions 4, 7, and 35 of the amino acid sequence, or an immunoglobulin-binding domain that, in addition of above substitution, has substitution of 1 to 6 amino acids with lysine at positions 40, 43, 46, 53, 54, and 56 of the amino acid sequence.

The present invention also encompasses the following multimeric immunoglobulin-binding proteins.

(1) A multimeric immunoglobulin-binding protein with an immunoglobulin-binding domain (R1) representing an amino acid sequence containing no lysine, and an immobilization binding domain (R2) in which all lysine residues in the amino acid sequence of the immunoglobulin-binding protein are substituted with non-lysine amino acids, and in which an amino acid sequence containing two or more lysine residues is added to the amino acid sequence terminal not attached to (R1).

(2) A multimeric immunoglobulin-binding protein with an immunoglobulin-binding domain (R1) representing an amino acid sequence containing no lysine, and a support immobilization binding domain (R2) representing the amino acid sequence of the immunoglobulin-binding protein, an amino acid sequence in which some of the lysine residues in the amino acid sequence of the immunoglobulin-binding protein are substituted with non-lysine amino acids, or an amino acid sequence in which some of the non-lysine amino acid residues are additionally substituted with lysine.

(3) A multimeric immunoglobulin-binding protein with an immunoglobulin-binding domain (R1) representing an amino acid sequence containing no cysteine, and an immobilization binding domain (R2) representing an amino acid sequence containing cysteine.

The present invention is also concerned with an insoluble support immobilizing a multimer in which a monomer (R2) having an immunoglobulin-binding domain or two linked monomers, that are immobilized on the insoluble support, occurs at the N- or C-terminus of a multimer of 5 or more linked monomers (R1) that have a single immunoglobulin binding site but are not involved in immobilization. The multimer is represented by the general formula (R1)n-(R2)m, or (R2)m-(R1)n. When the amino group of the lysine residue occurring in (R2) is used for immobilization on the insoluble support, oriented immobilization can be achieved when the lysine residues originally present in the amino acid sequence of (R1) are substituted with non-lysine amino acids in lysine residues the presence of which in the sequence compared to when these are absent in the sequence reduces the immunoglobulin-binding activity of the support yielded by the immobilization reaction with the insoluble support. Here, the (R2) domain may be a variant produced by using the method previously invented by the present inventors (PTL 1), specifically a variant in which a non-lysine amino acid has replaced the lysine residues originally present in the domain of protein A only at position 35, or at position 35 and one or more positions in positions 4, 7, and 35, or a variant in which 1 to 6 amino acids at positions 40, 43, 46, 53, 54, and 56 of the third α-helix that is not directly involved in immunoglobulin binding are additionally substituted with lysine.

When the lysine residues involved in covalent bonding in immobilization reaction in the amino acid sequence of the domain (R2) are all substituted with non-lysine amino acids, the amino group-mediated oriented immobilization can be achieved when an amino acid sequence containing two or more lysine residues is added to the amino acid sequence of (R2) at the terminal not attached to the (R1) domain. Here, only one lysine residue may be added; however, the immobilization rate can be improved by adding preferably two or more lysine residues. There are cases where the sequence portion excluding the amino acid sequence added to the terminal shares the same amino acid sequence as (R1). However, this does not affect the oriented immobilization.

Cysteine is introduced to the (R2) domain for oriented immobilization of the multimer via the thiol group of cysteine. Cysteine may be introduced by substituting any of the amino acids in the immunoglobulin-binding domain used as the (R2) domain. When using the immunoglobulin-binding domain of protein A, it is more preferable to introduce cysteine by substituting an amino acid in the third α-helix that is not directly involved in immunoglobulin binding. When adding a cysteine residue, it is preferable to use a method that adds cysteine or a cysteine-containing peptide to the N- or C-terminus. The protein may have a structure in which all the linked domains are (R1) domains, and cysteine or a cysteine-containing peptide is added to the N- or C-terminus. In such a structure, the (R1) domain with the added cysteine-containing sequence falls within the meaning of the (R2) domain used for immobilization.

The amino acid sequences of (R1) and (R2) may contain lysine residues when the protein is immobilized via a disulfide bond on a support having a thiol group. When an epoxy group is used to immobilize the thiol group, the domains may contain lysine residues, but a multimer that is more desirable for immobilization on an epoxy-activated support can be produced by introducing a cysteine residue as in (3) discussed above to the (R2) domain of the lysine-modified multimers described in (1) and (2) discussed above because an epoxy group shows relatively high reactivity to the amino group, though not as high as that of a thiol group.

The binding domains E, D, A, B, and C of *Staphylococcus* protein A may be used for the immunoglobulin-binding domain immobilized on the support of the present invention. The immunoglobulin-binding domain may have the amino acid sequence of any of the binding domains of *Staphylococcus*-derived protein A. However, it is preferable for lysine residue-mediated immobilization to use the alkali stable domain C having large numbers of lysine residues after position 39. It is also possible to use the sequence of domain Z that is widely used as an affinity ligand for immunoglobulins. It is, however, most preferable to use the sequence of C domain after substitution of glycine at position 29 with alanine, as this is known to improve chemical stability (the sequence represented by SEQ ID NO: 1 of Sequence Listing).

When the lysine residues are substituted with other amino acids for oriented immobilization of the immunoglobulin-binding domain, the substitution may be achieved with arginine, a basic amino acid having the same properties as lysine, as commonly performed in the art. Because the substitution is performed to eliminate the α-amino group having possible involvement with immobilization reaction, the oriented immobilization can be achieved through substitution of lysine with other amino acids, including arginine.

The present invention commonly uses the following methods.

[Overview of Immunoglobulin-Binding Protein Production]

A known gene recombinant technique, for example, such as the technique described in Frederick M. Ausubel, et al., Current Protocols In Molecular Biology may be used as the standard technique for the production of the immunoglobulin-binding protein of the present invention. Specifically, the immunoglobulin-binding protein of the present invention can be economically obtained in large quantities from cultured cells grown in a suitable liquid medium after transfecting a host cell such as *Escherichia coli* with an expression vector containing a nucleic acid sequence that codes for the target variant protein. More specifically, because a single immunoglobulin-binding domain of protein A is a small protein of about 60 amino acids, for example, a DNA that codes for the desired amino acid sequence is divided into synthetic oligonucleotides of several ten bases, and the synthesized DNA molecules are ligated with DNA ligase in a ligation reaction, and inserted into a plasmid vector to obtain the expression vector of interest. Here, it is common practice in the art to use a nucleic acid sequence with the optimal codon of *Escherichia coli* so that the protein is efficiently expressed in the bacteria. A mutation for achieving the desired amino acid substitution may easily be introduced to the intended site of the DNA sequence by using a method such as overlap extension, in which synthetic oligo DNAs that introduce mismatch base pairs are used as primers in polymerase chain reaction using unmodified clone DNA as a template. A mutation also may be introduced using cassette mutagenesis.

The cDNA that codes for the multimeric protein can easily be produced by introducing a recognition sequence of a restriction enzyme that recognizes the non-parindromic sequence to the ligation site between two cDNA domains of a dimer produced by joining cDNA that codes for a single immunoglobulin-binding domain (R1), and cDNA that codes for the amino acid sequence of a single domain (R2), and inserting an (R1)-coding cDNA fragment of the same sequence to this site using a ligation reaction. A multimeric protein with 6 or more linked immunoglobulin-binding domain units can easily be produced upon inserting the cDNA so produced into a suitable expression plasmid.

The nucleic acid sequence that codes for the variant protein of the present invention may be introduced to any expression vector that can replicate in the host cell, including, for example, plasmids, phages, and viruses. Examples of commercially available expression vectors include pQE vectors (Qiagen), pDR540, pRIT2T (GE Healthcare Bioscience), and pET vectors (Merck). Preferably, the expression vector is used in a suitably selected combination with the host cell. For example, when the host cell is *Escherichia coli*, it is preferable to use a pET vector with the BL21 (DE3) strain of *Escherichia coli*, or use a pDR540 vector with the JM109 strain of *Escherichia coli*.

The variant protein of the present invention may be collected by harvesting the cultured cells using a technique such as centrifugation, and disrupting the cells using, for example, ultrasonic waves or French press to allow the protein to collect in the soluble fraction. The variant protein may be purified by appropriately combining known separation and purification techniques. Specifically, it is possible to use separation techniques such as salting out, dialysis, and ultrafiltration, and purification techniques such as hydrophobic chromatography, gel filtration chromatography, ion exchange chromatography, affinity chromatography, and reversed phase chromatography.

[Overview of Immunoglobulin-Binding Protein Immobilization]

The material of the insoluble support that immobilizes the multimeric immunoglobulin-binding domain protein of the present invention is not particularly limited. The material may be, for example, a natural polymer material such as chitosan, dextran, cellulose, and agarose, or a synthetic polymer such as vinyl alcohol, polyimide, and methacrylate. In another embodiment, the material may be an inorganic support such as silica. The shape of the insoluble support is not particularly limited, and may have a form of, for example, a hollow fiber membrane, a monolith, or a bead. A bead-shaped insoluble support typically has a larger surface area per volume than membrane-like insoluble supports, and is suitable as an affinity support having high immunoglobulin binding capacity.

The support used for immobilization is, for example, a porous support with a plurality of pores. Because the multimer has a large space occupied volume, the pore size or the mesh structure of the porous support needs to provide a space volume sufficient for an immunoglobulin to easily approach and bind to the immobilized multimer. The exclusion limit of the porous support for the protein is preferably 1,000,000 to 200,000,000, more preferably 4,000,000 to 100,000,000. The support is preferably a bead-shape support with an average particle size of preferably 20 to 200 µm, more preferably 30 to 100 µm.

Typically, an affinity support is produced by immobilizing the protein on the support using a coupling agent such as cyanogen bromide, epichlorohydrin, N-hydroxysuccinimide, tosyl/tresyl chloride, carbodiimide, glutaraldehyde, and hydrazine, or a carboxyl or thiol activated support. Such coupling reactions are known in the art, and are well described in the literature (for example, Janson, J.-C., Ed. [Protein purification], 3rd edition, pp. 221-258, ISBN 978-0-471-74661-4). A feature of the multimeric immunoglobulin-binding domain protein of the present invention is that the protein is bound to the support via an amino acid residue that is disposed to enable orientational control, and the amino group-mediated immobilization may be achieved using a support having an active group, such as a tresyl group, an epoxy group, a carboxyl group, and a formyl group, that can form a covalent bond in a reaction with the amino group. Examples of commercially available supports include Toyopearl AF-Tresyl-650, Toyopearl AF-epoxy-650, Toyopearl AF-carboxy-650, and Toyopearl AF-formyl-650 (all available from Tosoh), NHS activated sepharose, cyanogen bromide activated sepharose, and epoxy-activated sepharose (all available from GE Healthcare Bioscience), Profinity Epoxide (Bio-Rad), Glyoxal Agarose (Agarose Bead Technologies), and Cellufine Formyl (JNC). For the immobilization of a cysteine residue via a thiol group, the GE Healthcare Bioscience product thiopropyl sepharose or epoxy-activated sepharose, and the Bio-Rad product Profinity Epoxide may be used.

The affinity support of the present invention produced in the manner described above is packed in a suitable column, and used in affinity chromatography for the isolation and purification of immunoglobulins such as IgA, IgG, and IgM.

The present invention is described below in greater detail using Examples. The present invention, however, is not limited by the following Examples.

Example 1

[Multimer Production Using C Domain of Lysine-Substituted *Staphylococcus*-Derived Protein A]

[Design and Construction of Variants]

Variants were designed and constructed using a method based on the method previously established by the present inventors (PTL 1). Specifically, a monomeric protein that can be orientationally immobilized at multiple points was produced by substituting the original lysine residues in a domain of protein A with a non-lysine amino acid only at position 35, or at position 35 and one or more positions in positions 4, 7, and 35, or by additionally substituting 1 to 6 amino acids with lysine at positions 40, 43, 46, 53, 54, and 56 of the third α-helix that is not directly involved in immunoglobulin binding.

A method that replaces a specific portion of a sequence with a sequence that codes for different amino acids in polymerase chain reaction (PCR) using a DNA fragment that codes for an amino acid sequence of a basic design is commonly practiced in the art. A cDNA fragment that has had substitution of its sequence at multiple locations can easily be obtained by repeating such a substitution procedure. PTL 1 describes a specific method for producing a variant protein in which the amino acid residues of specific positions are substituted with lysine residues, or in which the lysine residues of specific positions are substituted or deleted. Applicants of the present invention own a C' domain (SEQ ID NO: 1), a variant of the C domain of protein A in which the glycine at position 29 is substituted with alanine. By using the C' domain as a basic design, the present inventors constructed a multimer in which the immobilization binding domain (R2) containing lysine residues at the specific positions is linked to the C- or N-terminus of a multimer ((R1)n) of a structure including repeating n units of a domain variant (R1) in which all the lysine residues are substituted with some other amino acid, as follows.

First, a variant PN-95f (SEQ ID NO: 2) in which a non-lysine residue has replaced all the lysine residues originally present in positions 4, 7, 35, 42, 49, 50, and 58 of the C' domain was designed for (R1) domain. A cDNA fragment that codes for the amino acid sequence of PN-95f was then produced by performing a PCR using a C' domain coding DNA fragment as a template. A synthetic oligonucleotide corresponding to each modified portion was used as primer DNA. Separately, a variant PN-26f (SEQ ID NO: 3) was designed for (R2) domain, and a cDNA fragment that codes for the amino acid sequence of this variant was produced, using the same technique. The variant PN-26f was designed so that lysine residues were concentrated in the IgG non-binding region by the substitution of the all lysine residues with non-lysine amino acids at positions 4, 7, and 35 of the C' domain, and the substitution of the amino acid residues at positions 40, 43, 46, and 53 with lysine residues.

For the construction of the DNA that codes for the multimer, the PN-95f was designed so that the sequence began with a translation start codon containing a recognition sequence (CATATG) of restriction enzyme NdeI, and that a portion of the nucleic acid sequence that codes for glutamine-alanine-proline at positions 55 to 57 contained a recognition sequence (AGGCCCC) of restriction enzyme EcoO109I. A cDNA fragment for this sequence was prepared by PCR using the synthetic oligonucleotides of SEQ ID NOS: 4 and 5 as the forward and reverse primers, respectively. A cDNA fragment that codes for the amino acid sequence of PN-26f was produced by PCR using the following forward and reverse primers. As the forward primer, a synthetic oligonucleotide (SEQ ID NO: 6) was used that began with a common sequence for PN-26f and PN-95f following the PN-95f tail sequence containing the recognition sequence (AGGCCCC) of restriction enzyme EcoO109I. As the reverse primer, a synthetic oligonucleotide (SEQ ID NO: 7) of reverse direction was used that did not contain the recognition sequence of EcoO109I at positions 55 to 57 of the sequence, and that had a recognition sequence of restriction enzyme BamHI following a translation stop codon after the DNA sequence that codes for the last amino acid. The two DNA fragments that code for PN-95f and PN-26f were cut with restriction enzyme EcoO109I, and joined to each other to produce a cDNA that codes for a [PN-95f]-[PN-26f] dimer joined by the recognition sequence of EcoO109I. The dimeric cDNA fragment was subcloned into a pUC19 plasmid that had had the EcoO109I recognition sequence deleted beforehand.

By using the PN-95f coding cDNA fragment as template DNA, PCR was performed to produce a PN-95f cDNA fragment containing the recognition sequences of restriction enzyme EcoO109I on the both sides, using the synthetic oligonucleotides of SEQ ID NOS: 5 and 6.

The plasmid that codes for the [PN-95f]-[PN-26f] dimer joined with the recognition sequence of EcoO109I was cut with EcoO109I, and the cut ends were dephosphorylated with alkaline phosphatase. The PN-95f cDNA fragment containing the recognition sequences of EcoO109I on the both sides was then cut with EcoO109I, and the resulting fragment was inserted using a ligation reaction. The *Escherichia coli* DH-5a transfected with the product of the ligation reaction was inoculated on ampicillin-containing agar medium, and the clone from each colony appearing in the medium was cultured to analyze the plasmid of each clone. The clones were identified as a tetrameric cDNA of the form [PN-95f]-[PN-95f]-[PN-95f]-[PN-26f] ([PN-95f]$_3$-[PN-26f]) when two PN-95f cDNA fragments containing the recognition sequences of EcoO109I on the both sides were inserted at the EcoO109I recognition sequence portion between [PN-95f]-[PN-26f], and a pentameric cDNA when three PN-95f cDNA fragments were inserted ([PN-95f]$_4$-[PN-26f]). The clones were identified as hexameric, octameric, decameric, and dodecameric cDNAs when 4, 6, 8, and 10 PN-95f cDNA fragments were inserted, with the PN-26f occurring only at the C-terminus. The tetramer, pentamer, hexamer, octamer, decamer, and dodecamer so obtained were named PN-421, PN-521, PN-621, PN-821, PN-1021, and PN-1221, respectively.

For the production of cDNA for the hexamer PN-623 ([PN-95f]$_5$-[PN-99f]) in which the tail end PN-26f is replaced with PN-99f that differed from PN-95f in that the lysine residue occurred only at position 58, the cDNA that codes for the [PN-95f]-[PN-99f] dimer linked at the recognition sequence of EcoO109I was first subcloned into the pUC19 plasmid that has had the EcoO109I recognition sequence deleted beforehand, and a clone was selected in which four PN-95f cDNA fragments that had the EcoO109I recognition sequences on the both sides were inserted at the EcoO109I recognition site between [PN-95f]-[PN-99f], in the manner described above.

For the production of cDNA for the hexamer PN-651 ([PN-26f]-[PN-95f]$_5$) in which a single domain variant PN-26f with the concentrated lysine residues was disposed at the N-terminus, and in which five domain variants PN-95f containing no lysine residues were joined to the C-terminus, a cDNA that codes for the [PN-26f]-[PN-95f] dimer linked at the recognition sequence of EcoO109I was first subcloned into the pUC19 plasmid that has had the EcoO109I recognition sequence deleted beforehand, and a clone was selected in which four PN-95f cDNA fragments that had the EcoO109I recognition sequences on the both sides were inserted at the EcoO109I recognition site, in the manner described above.

The pUC19 plasmid subcloned with each multimeric cDNA obtained in the manner described above was treated with restriction enzymes NdeI and BamHI to cut each cDNA fragment, and the cDNA fragment was inserted into the *Escherichia coli* expression vector pET9a to construct an expression plasmid. The nucleic acid sequence of each expression plasmid was then analyzed using a CEQ-8000 DNA sequencer (Beckman Coulter). The analysis confirmed that the plasmid had the sequence as designed. The expression plasmids were used to transform BL21 (DE3) competent cells (Merck), and multimeric protein-expressing strains were obtained.

The *Escherichia coli* strain expressing each multimeric protein was seed-cultured for 12 h in LB medium containing 25 mg/L kanamycin and 2.0% glucose. The seed-cultured liquids were inoculated in a 2×TY medium containing 25 mg/L kanamycin and 0.8% glucose, and cultured at 37° C. for 16 h to express the protein of interest, and then the *Escherichia coli* were collected by centrifugation. The collected *Escherichia coli* were then suspended in a 50 mM MES buffer (pH 6.0), and disrupted by sonication. The protein was then collected into the supernatant by centrifugation. Each supernatant as a bacteria extract was subjected to sodium dodecylsulfate (SDS)-polyacrylamide gel electrophoresis. The electrophoresis confirmed production of the protein of interest of the expected molecular weight.

[Purification and Purity Assay of Modified Multimer]

Figure 1:
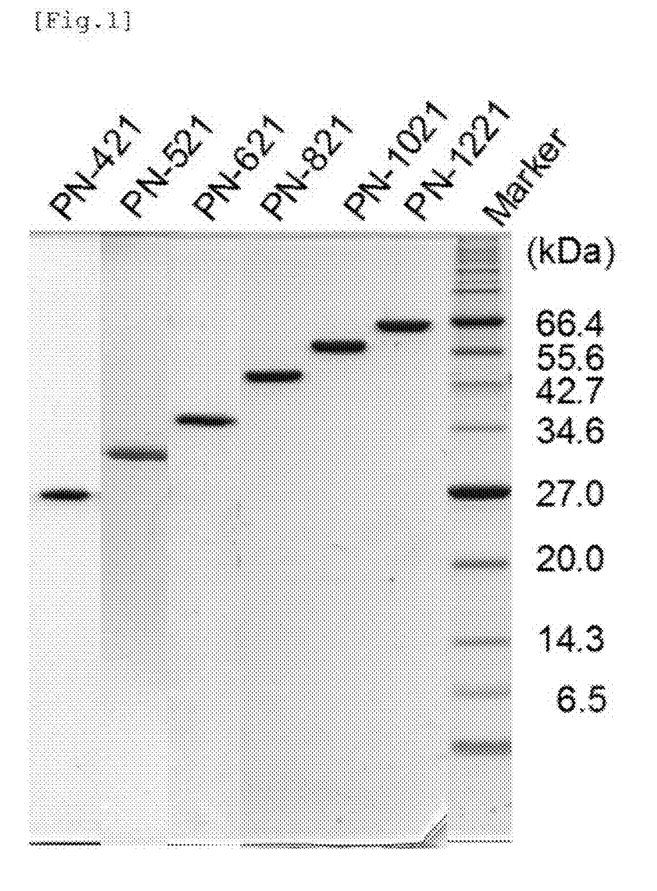
FIG. 1 represents the result of SDS-polyacrylamide gel electrophoresis performed for various purified multimers.

The cell extract of each modified multimer was applied to a cation exchanger SP-Sepharose Fast Flow (GE Healthcare Bioscience) column after being adjusted to pH 5.2. The column was washed with a 20 mM phosphate buffer (pH 6.0), and elution from the column was carried out with increasing NaCl concentrations. It was confirmed that elution of all multimers occurred between 0.1 and 0.2 M NaCl. The eluate containing the multimer was then added to an anion exchanger GigaCap Q (Tosoh) column after being adjusted to pH 9. The column was washed with a 20 mM phosphate buffer (pH 7.8), and multimer was eluted with 0.3 M NaCl. The eluate was subjected to SDS-polyacrylamide gel electrophoresis to confirm purity. The multimers occurred as single bands at positions corresponding to the theoretical molecular weights, confirming each multimer being purified (FIG. 1).

[Immobilization on Gel Support, and Immunoglobulin Binding Amount Measurement for Evaluation]

Figure 2:
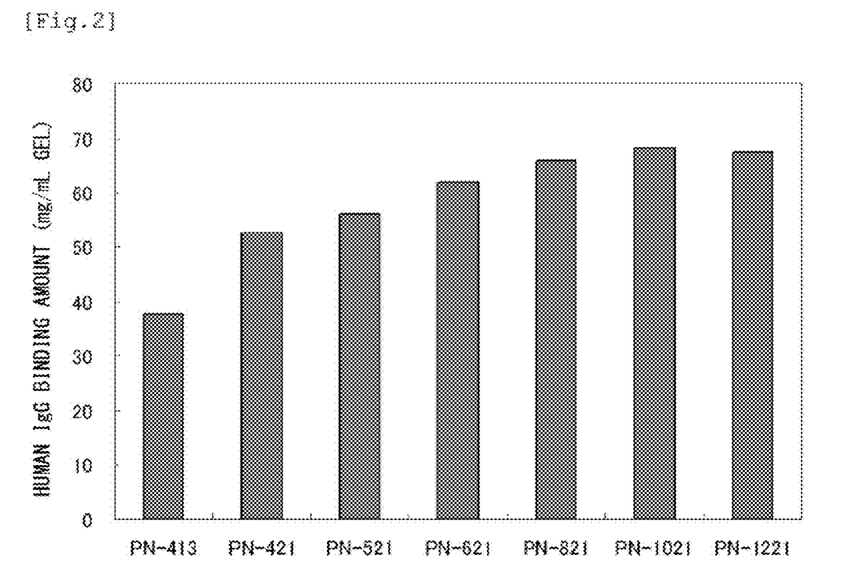
FIG. 2 represents the result of the comparison of the human IgG binding capacity of Toyopearl AF-formyl-650 immobilizing various multimers.

A solution of each purified immunoglobulin-binding protein of the present invention was subjected to immobilization on a chemically synthesized polymer gel support Toyopearl AF-formyl-650 (Tosoh) at a concentration of 10 mg/mL gel using an ordinary method. Separately, a solution of a tetramer (PN-413) with four linked PN-26f (R2) domains all involved in immobilization was also subjected to immobilization under the same conditions after purifying the tetramer in the manner described above. The reaction solution after immobilization was collected, and measured for immobilization rate. All multimers had an immobilization efficiency of 90% or more. The gel support after the immobilization reaction was washed with a PBS solution, and shaken for 1 h after adding a PBS solution containing 40 mg/mL of human IgG. The human IgG that bound to the gel support was then eluted from the PBS-washed gel support, using a 0.1 M glycine hydrochloride buffer (pH 2.8). The eluate was measured for absorbance at 280 nm with a spectrophotometer, and the binding amounts of immunoglobulin were determined using a specific absorption coefficient of 13.8 (1 $g^{-1} \times cm^{-1}$). FIG. 2 represents the immunoglobulin binding amount (mg) of each multimer per milliliter of the gel. The multimers with the (R2) domain occurring at the C-terminus all showed high binding capacity compared to the non-oriented tetramer PN-413. The binding amounts of the pentamer (PN-521), hexamer (PN-621), octamer (PN-821), decamer (PN-1021), and dodecamer (PN-1221) were 1.06, 1.18, 1.25, 1.29, and 1.28 times, respectively, greater than the binding amount of the tetramer (PN-421) that had the (R2) domain at the C-terminus. As can be seen from these results, the immunoglobulin binding amount increased with increasing numbers of the repeating domains in multimers that were orientationally immobilized on the support with the immobilization sites concentrated in the single C-terminal domain.

Figure 3:
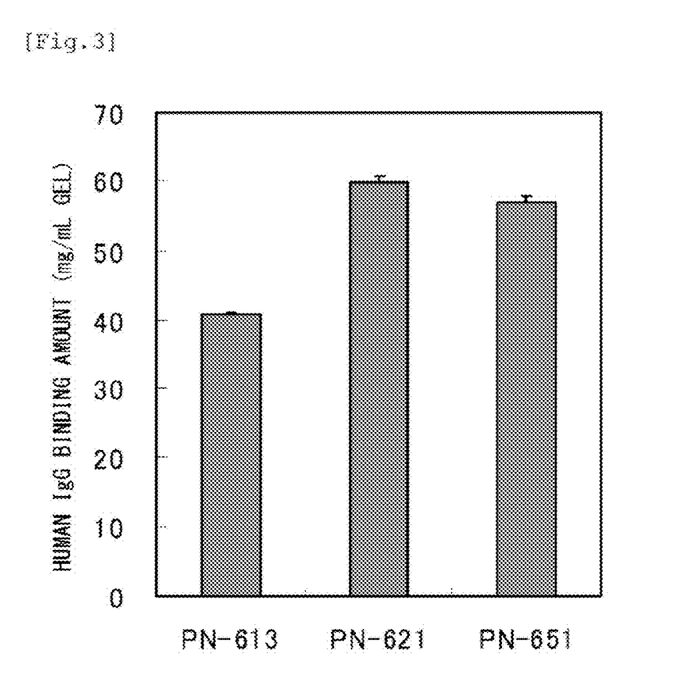
FIG. 3 represents the result of the comparison of the human IgG binding capacity of Toyopearl AF-formyl-650 immobilizing different hexamers PN-613, 621, and 651.

A variant ((R2)m-(R1)n) in which the (R2) domain is disposed on the N-terminal side of a multimer ((R1)n) with the repeated (R1) domains was produced in the same manner described above, and immobilized on a Toyopearl AF-formyl-650 gel support. The immobilizing gel support was measured for human IgG binding capacity in the manner described above, and an increased binding amount was confirmed as in the multimers in which the (R2) domain was disposed at the C-terminus. As an example, FIG. 3 represents the result of the comparison of human IgG binding capacity between hexamer PN-613 containing six linked (R2) domains, hexamer PN-621 containing the (R2) domain disposed at the C-terminus, and hexamer PN-651 containing the (R2) domain disposed at the N-terminus. As can be seen in the figure, the binding capacity clearly increased in both cases that the (R2) domain was disposed at the C-terminus or the N-terminus of the multimer.

Figure 4:
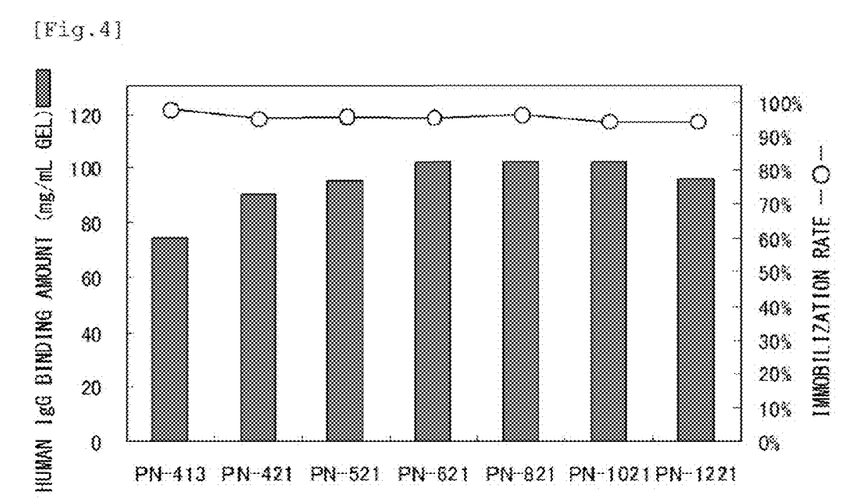
FIG. 4 represents the results of the comparison of immobilization rate, and the comparison of the human IgG binding capacity of agarose immobilizing 10 mg/mL of various multimers.

The tetrameric, pentameric, hexameric, octameric, decameric, and dodecameric modified multimers of the present invention were immobilized on a formyl-activated natural-polymer 6% crosslinked agarose gel support at a concentration of 10 mg/mL gel using an ordinary method. For comparison, PN-413 was also immobilized under the same conditions. The reaction liquid after the immobilization was measured for multimer amount, and the immobilization rate was 95% or more in all multimers (FIG. 4). FIG. 4 represents the measured IgG binding amounts (mg/mL gel) on the immobilizing gel support. The multimers of the present invention with the terminal immobilization domain all showed higher binding amounts than PN-413 as with the case using the Toyopearl AF-formyl-650 gel support. The hexamer (PN-621) showed a binding amount 1.37 times higher than that of PN-413. The binding amounts of the octamer (PN-821) and the decamer (PN-1021) were about the same as the binding amount of the hexamer. The binding amount of the dodecamer (PN-1221) was 94% of the binding amount of the hexamer (PN-621). The binding amount of the pentamer (PN-521) was 1.05 times higher than the binding amount of the tetramer (PN-421). The hexamer, the octamer, and the decamer showed binding amounts that were 1.13 times the binding amount of the tetramer. Considering that the immobilization rate of each variant for the gel support was almost constant at 95% or more, it was considered preferable to immobilize the hexamer, the octamer, and the decamer for the production of a gel support that exhibits the optimum IgG binding amount. The multimers used at 10 mg/mL gel for immobilization are all equivalent of 1.45 μmol domain/mL gel in terms of the amount of the immunoglobulin-binding domain. A calculation based on immobilization rate yields an immobilization domain amount of 1.38 mol domain/mL gel for the hexamer. Here, because the human IgG binding amount was 0.7 μmol/mL gel, the IgG binding amount ratio per binding domain was 0.51. Specifically, this shows that three molecules of IgG bind per molecule of the hexamer, confirming that one IgG molecule binds per two domains.

Figure 5:
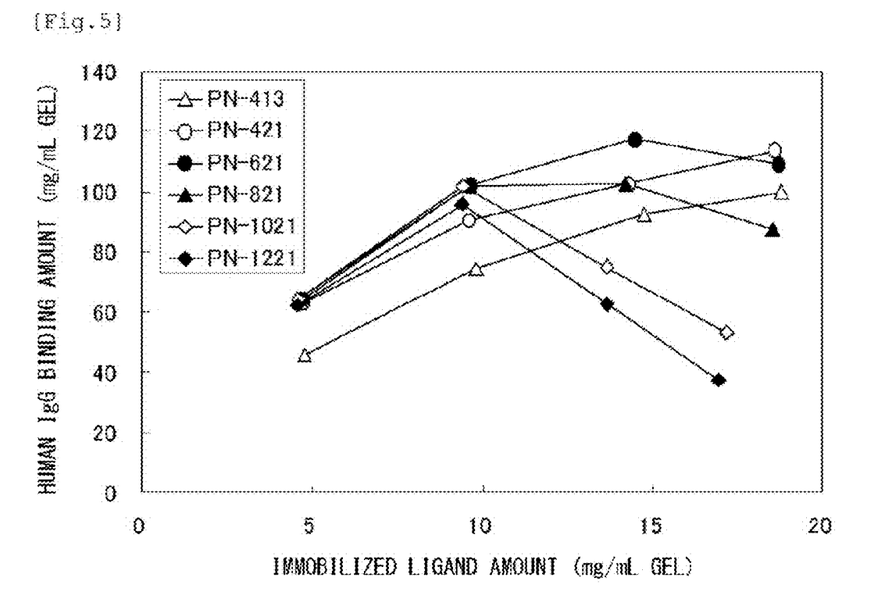
FIG. 5 represents the result of the comparison of the human IgG binding amounts of supports immobilizing various multimers at different immobilization amounts.

For detailed comparison, the tetrameric, hexameric, octameric, decameric, and dodecameric variants were immobilized on formyl-activated 6% crosslinked agarose gel supports at varying immobilization reaction concentrations of 5, 10, 15, and 20 mg/mL gel, and measured for immobilized multimer amount, and the human IgG binding amount of the immobilizing gel support (FIG. 5). The measured values for PN-413 are also shown for comparison in FIG. 5. All modified multimers had higher binding amounts than PN-413 at 5 mg/mL gel and 10 mg/mL gel, and the immunoglobulin binding amount increased in proportion to the immobilization amount on the gel support. The decamer (PN-1021) and the dodecamer (PN-1221) showed the maximum values at 10 mg/mL gel, and the binding amounts decreased at a concentration of 15 mg/mL gel or more. The octamer (PN-821) showed about the same maximum values at 10 mg/mL and 15 mg/mL. The binding amount of the hexamer (PN-621) increased with increasing concentrations, and reached the maximum value at 15 mg/mL. The binding amount of the tetramer (PN-421) gradually increased with increasing concentrations up to 20 mg/mL. The hexamer (PN-621) showed the highest binding amount with the least immobilization amount. From these results, it was confirmed that the hexamer, the octamer, and the decamer, when immobilized in 10 mg/mL gel, can be used to produce a gel support having higher antibody binding capacity than that produced with the tetramer. Particularly, the hexamer (PN-621), when immobilized on the gel support in 15 mg/mL gel, was shown to be capable of producing an affinity gel support having a desirably high binding amount 1.15 times higher than that achieved with the tetramer (PN-421).

Example 2

[Production of Multimer with (R1) Using C Domain Having Substitution of Lysine Residue at Positions 4, 7, and 35]
[Design and Construction of Modified Multimer]

In Example 1, the C' domain used as (R1) domain had all of its lysine residues substituted. Example 2 focused on the lysine residues at positions 4, 7, and 35 out of the seven lysine residues originally present in the C' domain, and produced a multimer that contained the (R1) domain for which the C' domain that had had the substitution of each lysine residue at these three positions with non-lysine amino acids was used. The multimers were then compared for the effect of the substitution on the immunoglobulin-binding activity of the support yielded by immobilization reaction. The following method was used to construct a hexamer in which the substituted C' domain was used as the repeating unit of five linked (R1) domains, and in which PN-26f was linked as (R2) to the C-terminus.

The variant was designed and constructed using the method described in Example 1. Specifically, for the production of a cDNA for [C']$_5$-[PN-26f](PN-661), a cDNA that codes for the [C']-[PN-26f] dimer linked with the recognition sequence of EcoO109I was first subcloned into a pUC19 plasmid that had had the EcoO109I recognition sequence deleted beforehand, and a clone was selected in which four [C'] cDNA fragments that had the EcoO109I recognition sequences on the both sides were inserted at the EcoO109I recognition site between [C']-[PN-26f]. In the same manner, PN-662, PN-663, and PN-664 cDNAs were produced by selecting clones in which four [PN-23f](SEQ ID NO: 8), [PN-87f](SEQ ID NO: 12), and [PN-61f](SEQ ID NO: 10) cDNA fragments that had the EcoO109I recognition sequences on the both sides were inserted at the EcoO109I recognition site of the cDNAs that code for [K35R-C'(PN-23f)]-[PN-26f], [K4A,K35R-C' (PN-87f)]-[PN-26f], and [K4A,K7T,K35R-C' (PN-61f)]-[PN-26f] dimers.

The plasmids were treated with restriction enzymes NdeI and BamHI to cut each cDNA fragment, which was then inserted into the *Escherichia coli* expression vector pET9a to construct an expression plasmid of each hexamer.

The multimeric cDNAs obtained in the manner described above were used to construct expression plasmids using the same method used in Example 1, and the nucleic acid sequence of each plasmid was analyzed using a DNA sequencer. The analysis confirmed that the plasmid had the sequence as designed. The expression plasmids were used to transform BL21 (DE3) competent cells, and multimeric protein-expressing strains were obtained. The respective expressing strains were cultured in the manner described in Example 1 to express the proteins of interest. The resulting *Escherichia coli* cells were disrupted, and subjected to SDS-polyacrylamide gel electrophoresis. The electrophoresis confirmed production of the protein of interest of the expected molecular weight.

[Purification and Purity Assay of Modified Multimer]

The multimer was purified from the cell extract of each modified multimer in the same manner as in Example 1, and the purity was confirmed by SDS-polyacrylamide gel electrophoresis. The multimers occurred as single bands at positions corresponding to the theoretical molecular weights.

[Immobilization on Gel Support, and Immunoglobulin Binding Amount Measurement for Evaluation]

The purified multimers were each immobilized on a formyl-activated 6% crosslinked agarose gel support at a concentration of 10 mg/mL gel in the same manner as in Example 1, and measured for immobilized multimer amount, and the human IgG binding amount of the immobilizing gel support. The reaction liquid after the immobilization was measured for multimer amount. The immobilization was desirable with all multimers showing the desirably high immobilization rate of 95% or more. Human IgG (40 mg/mL) was reacted with the gel support immobilizing each multimer, and the bound IgG was eluted from the gel support to measure the binding amount (Table 1). The PN-662 that had the substitution of the lysine residue with arginine at position 35 had a binding amount 1.07 times higher than the binding amount of the PN-661 that had the (R1) domain for which the C' domain was used in native-form without lysine substitution. The PN-663 in which alanine replaced the lysine residue at position 4, and the PN-664 in which alanine and threonine replaced the lysine residues at positions 4 and 7 in addition to the substitution in PN-662 had binding amounts that were 1.20 times and 1.42 times higher, respectively, than the binding amount of PN-661. The PN-621 in which all lysine residues in the C domain were substituted with other amino acids had a binding amount 1.63 times higher than that of PN-661. The PN-664 and PN-621 were shown to yield about the same levels of binding amount in reactions of the multimer immobilizing gel supports with human IgG used in 8 mg/mL, a concentration close to the actual concentration range of human IgG purification (Table 1). As clearly demonstrated in Example 1, oriented immobilization on the gel support increases the IgG binding capacity when the (R1) domain is a domain in which all of the seven lysine residues present in the C domain are substituted with non-lysine amino acids. The results of Example 2 showed that the substitution of the original lysine residue of the C domain with other amino acids at positions 4, 7 and/or 35 was also effective at increasing the IgG binding amount. It is believed that the substitution of these C domain lysine residues with other amino acids increased the binding amount through enhanced oriented immobilization of the multimer. The immunoglobulin-binding activity of PN-613, that contained six linked PN-26f domains as (R2) having the substitution of lysine residues with other amino acids at positions 4, 7, and 35, and in which lysine residues were introduced to the third α-helix through substitution to increase the immobilization capability as described in Example 1, was about 65% of the immunoglobulin-binding activity of PN-621, and in this case, PN-613 was immobilized on the gel support without being oriented. From the result that the binding amount of PN-661 was about 62% of the binding amount yielded by PN-621, it can be said that the PN-661 was immobilized without being oriented. Specifically, the C domain used as (R1) domain can achieve immunoglobulin-binding activity enhanced immobilization when 1 to 3 of the lysine residues originally present in the sequence are substituted at positions 4, 7, and 35, without substituting all the lysine residues with other amino acids.

TABLE 1

Comparison of binding capacity of multimers containing (R1) that uses C domain having substitution of different lysine residues

| | Human IgG binding amount (mg/mL gel) | |
|---|---|---|
| | 40 mg/mL | 8 mg/mL |
| PN-661 (R1 = 4K7K35K42K49K50K58K, C') | 62.9 (100) | 57.5 (100) |
| PN-662 (R1 = 4K7K35R42K49K50K58K) | 67.1 (107) | 62.6 (109) |
| PN-663 (R1 = 4A7K35R42K49K50K58K) | 75.2 (120) | 69.0 (120) |
| PN-664 (R1 = 4A7T35R42K49K50K58K) | 89.5 (142) | 79.3 (138) |
| PN-621 (R1 = 4A7T35R42R49R50R58R) | 102.3 (163) | 80.9 (141) |

Example 3

[Production of Multimer Containing (R2) that Uses C Domain Containing Lysine Residues Introduced by Substitution]

[Design and Construction of Modified Multimer]

By using the method described in Example 1, a hexamer PN-667 was produced that contained (R1) for which a C domain that had had all of its lysine residues substituted with other amino acids was used, and (R2) that contained a total of six lysine residues after the additional substitution of lysine residues at positions 54 and 56 in the (R2) domain of Example 1. For this purpose, a PN-28f was produced by additionally substituting the lysine residues at positions 54 and 56 of the PN-26f used in Example 1. The PN-28f (SEQ ID NO: 9) was disposed at the C-terminus to produce the hexamer PN-667 that contained five linked (R1) domains of PN-95f described in Example 1.

The lysine residues originally present in positions 4, 7, and 35 of the C domain were substituted with some other amino acid only at position 35, and lysine was introduced to positions 40, 43, 46, and 53 through substitution to produce a domain PN-83f (SEQ ID NO: 11). This domain was used as (R2) to produce a hexamer PN-669. The PN-669 had the same (R1) domain contained in PN-621.

The variants were designed and constructed in the same manner as in Example 1. Specifically, for the production of a cDNA for [PN-95f]$_5$-[PN-28f](PN-667), a cDNA that codes for the [PN-95f]-[PN-28f] dimer linked with the recognition sequence of EcoO109I was first subcloned into a pUC19 plasmid that had had the EcoO109I recognition sequence deleted beforehand, and a clone was selected in which four [PN-95f] cDNA fragments that had the EcoO109I recognition sequences on the both sides were inserted at the EcoO109I recognition site between [PN-95f]-[PN-28f]. A PN-669 cDNA was produced by selecting a clone in which four [PN-95f] cDNA fragments that had the EcoO109I recognition sequences on the both sides were inserted at the EcoO109I recognition site of the cDNA that codes for the [PN-95f]-[PN-83f] dimer.

The multimeric cDNAs obtained in the manner described above were used to construct expression plasmids using the same method used in Example 1, and the nucleic acid sequence of each plasmid was analyzed using a DNA sequencer. The analysis confirmed that the plasmid had the sequence as designed. The expression plasmids were used to transform BL21 (DE3) competent cells, and multimeric protein-expressing strains were obtained. The respective expressing strains were cultured in the manner described in Example 1 to express the proteins of interest. The resulting *Escherichia coli* cells were disrupted, and subjected to SDS-polyacrylamide gel electrophoresis. The electrophoresis confirmed production of the proteins of interest at positions corresponding to the respective expected molecular weight.

[Purification and Purity Assay of Modified Multimer]

The multimer was purified from the cell extract of each modified multimer in the same manner as in Example 1, and the purity was confirmed by SDS-polyacrylamide gel electrophoresis. The multimers occurred as single bands at positions corresponding to the theoretical molecular weights.

[Immobilization on Gel Support, and Immunoglobulin Binding Amount Measurement for Evaluation]

The purified multimers were each immobilized on a formyl-activated 6% crosslinked agarose gel support at a concentration of 10 mg/mL gel in the same manner as in Example 1, and measured for immobilized multimer amount, and the human IgG binding amount of the immobilizing gel support. The reaction liquid after the immobilization was measured for multimer amount. The immobilization was desirable with all multimers showing the desirably high immobilization rate of 95% or more. Human IgG (40 mg/mL) was reacted with the gel support immobilizing each multimer, and the bound IgG was eluted from the gel support to measure the binding amount (Table 2). The PN-667 had a human IgG binding amount of 102 mg/mL gel, the same amount observed for PN-621. The PN-669 had the same level of binding capacity as PN-621. The binding capacity of the multimers was PN-621=PN-669>PN-667 in a reaction of 8 mg/mL of human IgG with the gel support immobilizing each multimer. It was found from these results that the IgG binding activity is not inhibited even when the (R2) domain has all of the six amino acid residues at positions 40, 43, 46, 53, 54, and 56 of the C domain substituted with lysine, and that such a variant shows the same level of IgG binding amount as PN-621 in which lysine has replaced the four lysine residues at positions 40, 43, 46, and 53. The result that the immobilization for the gel support was higher in PN-667 than in PN-621 (97% vs. 95%) suggests that increasing the number of lysine substitutions is advantageous for the immobilization of (R2). On the other hand, the binding test using low-concentration IgG (8 mg/mL) revealed that the substitution of four lysine residues as in PN-621 was more desirable for binding of low-concentration IgG than substituting six lysine residues as in PN-667. From the results for PN-621 and PN-669 shown in Table 2, it can be seen that the lysine-introduced modified domain produced through substitution from the C domain can be used as (R2) domain for oriented immobilization after the substitution of the original lysine residues at positions 4 and 7 with other amino acids, or even without the substitution of these lysine residues.

TABLE 2

Comparison of binding capacity of multimers containing (R2) that uses C domain containing lysine residues introduced by substitution

| | Human IgG binding amount (mg/mL gel) | |
|---|---|---|
| | 40 mg/mL | 8 mg/mL |
| PN-621 (R2 = 4A7T35R40K43K46K53K) | 102.3 | 80.9 |
| PN-667 (R2 = 4A7T35R40K43K46K53K54K56K) | 102.0 | 78.7 |
| PN-669 (R2 = 35R40K43K46K53K) | 102.3 | 81.0 |

Comparative Example 1

Commercially available gel supports orientationally immobilizing multimeric proteins, and gel supports immobilizing the multimer of the present invention were compared for human IgG binding capacity. For comparison, a gel support product in which native sequence protein A with the introduced C-terminal cysteine is immobilized on an epoxy-activated crosslinked agarose gel support was used as a pentamer-immobilized support (rProtein A-Sepharose FF, GE Healthcare Science). As a tetramer-immobilized support, a gel support product was used in which a tetramer of four linked Z domains of protein A with the introduced C-terminal cysteine residue is immobilized on an epoxy-activated crosslinked agarose gel support (MabSelect SuRe, GE Healthcare Science). As can be seen in Table 3, comparisons with these commercially available products confirmed that the agarose gel support immobilizing the hexamer (PN-621) of the present invention had higher IgG binding capacity. Here, the binding amounts of rProtein A-Sepharose FF and PN-621 were compared at the same multimer concentrations at 6 mg/mL gel in accordance with the concentration used in rProtein A-Sepharose FF, as shown in Table 3.

TABLE 3

Comparison of hexamer of the present invention with commercially available products

| | Human IgG binding amount (mg/mL gel) |
|---|---|
| rProtein A-Sepharose FF | 50.1 |
| MabSelect SuRe | 45.5 |
| Hexamer (PN-621)-immobilized agarose (6 mg/mL) | 72.0 |
| Hexamer (PN-621)-immobilized agarose (10 mg/mL) | 102.2 |

Comparative Example 2

<Immobilization Domain with Single Terminal-Lysine Residue>

The PN-95f that had all the lysine residues substituted with other amino acids as in Example 1 were linked to each other to produce a hexamer (PN-623) of six PN-95f domains conserving only one lysine residue at the C-terminus of the multimer. This protein was compared with the hexamer (PN-621) of the present invention, and these were measured for the human IgG binding amount of the formyl-activated 6% crosslinked agarose gel supports immobilizing these hexamers in 10 mg/mL gel. As can be seen in the result of comparison shown in Table 4, the PN-623 containing one lysine residue at the C-terminus had 34.5% of the human IgG binding amount yielded by PN-621. The result suggests that it is more desirable to introduce two or more lysine residues to the (R2) domain. From the previous finding that the N-terminal α-amino group has low reactivity, and that acetylation of the α-amino group has no effect on immobilization of the variant, it was concluded in this comparative example that the amino group involved in immobilization was the C-terminal lysine residue.

TABLE 4

Binding capacity of hexamers after introduction of one lysine residue

| | Human IgG binding amount (mg/mL gel) |
|---|---|
| Hexamer (PN-623)-immobilized agarose | 34.9 |
| PN-621-immobilized agarose | 101.1 |

Example 4

[Production of Multimer Containing (R2) with Added Lysine at C-Terminus of C Domain]
[Design and Construction of Modified Multimer]

By using the method described in Example 1, a hexamer PN-666 was produced that contained five linked (R1) domains modified by substituting the lysine residues of the C domain with other amino acids, and an (R2) domain modified by substituting the all lysine residues of the C domain with other amino acids except for the C-terminal lysine residue, and adding lysine to the C-terminus. The (R2) domain of the PN-666 had the same sequence as the (R1) domain, except for the sequence added to the C-terminus.

[Purification and Purity Assay of Modified Multimer]

The multimer was purified from the cell extract of the modified multimer in the same manner as in Example 1, and the purity was confirmed by SDS-polyacrylamide gel electrophoresis. The multimer occurred as a single band at a position corresponding to the theoretical molecular weight.

[Immobilization on Gel Support, and Immunoglobulin Binding Amount Measurement for Evaluation]

The purified multimer was immobilized on a formyl-activated 6% crosslinked agarose gel support at a concentration of 10 mg/mL gel in the same manner as in Example 1, and measured for immobilized multimer amount, and the human IgG binding amount of the immobilizing gel support. The reaction liquid after the immobilization was measured for multimer amount. The immobilization was desirable with the multimer showing the desirably high immobilization rate of 95% or more. Human IgG (40 mg/mL) was reacted with the gel support immobilizing the multimer, and the bound IgG was eluted from the gel support to measure the binding amount. The PN-666 had about the same human IgG binding amount as PN-621, which yielded a human IgG binding amount of 102 mg/mL gel. The immunoglobulin binding amount was PN-621=PN-669>PN-667>PN-666 in a reaction of 8 mg/mL of human IgG with the gel support immobilizing the multimer. It was found from these results that oriented immobilization is possible when the sequence at the C-terminus of the (R2) domain is a lysine-concentrated sequence added to the C-terminus and containing more than one lysine residue, an amino acid used for immobilization.

INDUSTRIAL APPLICABILITY

A support immobilizing the multimer of the general formula (R1)n-(R2)m or (R2)m-(R1)n of the present invention can be used as a low-cost immunoglobulin-binding affinity support having high binding capacity. The support has many applications, including immunoglobulin production in the field of antibody drugs or antibody diagnostic drugs, removal of immunoglobulins from biological components, and component analysis.

---

The invention claimed is:

1. An immunoglobulin-binding protein as a multimer of immunoglobulin binding domains represented by the following general formula:

(R1)$n$-(R2)$m$, or (R2)$m$-(R1)$n$, wherein R2 is an immunoglobulin-binding domain occurring at the N-terminus or the C-terminus of the protein, and that includes an amino acid residue that covalently bonds to an insoluble support upon immobilization reaction with the insoluble support, and R1 is an immunoglobulin-binding domain that does not contain an amino acid residue the presence of which in the sequence compared to when it is absent in the sequence reduces the immunoglobulin-binding activity of the support yielded by the immobilization reaction, the immunoglobulin-binding domains comprising an amino acid sequence with the left end representing the N-terminus and the right end representing the C-terminus, the immunoglobulin-binding protein having properties that satisfy the following conditions, and that allow the immunoglobulin-binding protein to be immobilized on the insoluble support via the amino acid residue of the (R2) domain:

(1) n is an integer of 5 to 9;
(2) m is an integer of 1 or 2;
(3) the n (R1) domains may or may not have the same sequence; and
(4) the total number of domains (n+m) is 6 to 10, wherein the immunoglobulin-binding domains (R1) and (R2) each comprise a domain modified from the amino acid sequence of an immunoglobulin-binding domain of *Staphylococcus* protein A, wherein the (R1) domain of the general formula comprises an amino acid sequence of the immunoglobulin-binding domain of *Staphylococcus* protein A in which the lysine residues originally present in the sequence are substituted with a non-lysine amino acid at 1 to 3 of positions 4, 7, and 35, and without any amino acid substitution with a lysine residue, and wherein the (R2) domain of the general formula comprises an amino acid sequence of the immunoglobulin-binding domain of *Staphylococcus* protein A which includes substitution of 1 to 6 amino acid residues with lysine at positions 40, 43, 46, 53, 54, and 56.

2. The immunoglobulin-binding protein according to claim 1, wherein the (R2) domain further comprises substitutions of the original lysine residues with a non-lysine amino acid (i) at position 35, or (ii) at position 35 and one or more of positions 4 and 7.

3. The immunoglobulin-binding protein according to claim 2, wherein the (R1) domain further comprises substitutions of the original lysine residues with a non-lysine amino acid at 1 to 4 of positions 42, 49, 50, and 58.

4. An immunoglobulin-binding immobilization support comprising the immunoglobulin-binding protein of claim 1 immobilized on an insoluble support.

5. A method for separating and purifying an immunoglobulin comprising contacting a solution comprising the immunoglobulin with the immunoglobulin-binding immobilization support of claim 4.

6. An immunoglobulin-binding immobilization support comprising the immunoglobulin-binding protein of claim 2 immobilized on an insoluble support.

7. A method for separating and purifying an immunoglobulin comprising contacting a solution comprising the immunoglobulin with the immunoglobulin-binding immobilization support of claim 6.

8. An immunoglobulin-binding immobilization support comprising the immunoglobulin-binding protein of claim 3 immobilized on an insoluble support.

9. A method for separating and purifying an immunoglobulin comprising contacting a solution comprising the immunoglobulin with the immunoglobulin-binding immobilization support of claim 8.

* * * * *

SEQUENCE LISTING

<160> NUMBER OF SEQ ID NOS: 12

<210> SEQ ID NO 1
<211> LENGTH: 58
<212> TYPE: PRT
<213> ORGANISM: Staphylococcus aureus
<220> FEATURE:
<223> OTHER INFORMATION: Protein A mutated immunoglobulin-binding
      domain(C-domain + G29A)

<400> SEQUENCE: 1

Ala Asp Asn Lys Phe Asn Lys Glu Gln Gln Asn Ala Phe Tyr Glu Ile
                5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: modified immunoglobulin-binding protein(PN-95f)

<400> SEQUENCE: 2

Ala Asp Asn Ala Phe Asn Thr Glu Gln Gln Asn Ala Phe Tyr Glu Ile
                5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg Arg Leu Asn Asp Ala Gln Ala Pro Arg
    50                  55

<210> SEQ ID NO 3
<211> LENGTH: 58
<212> TYPE: PRT
<213> ORGANISM: Artificial Sequence
<220> FEATURE:
<223> OTHER INFORMATION: modified immunoglobulin-binding protein(PN-26f)

<400> SEQUENCE: 3

Ala Asp Asn Ala Phe Asn Thr Glu Gln Gln Asn Ala Phe Tyr Glu Ile
                5                   10                  15

Leu His Leu Pro Asn Leu Thr Glu Glu Gln Arg Asn Ala Phe Ile Gln
            20                  25                  30

Ser Leu Arg Asp Asp Pro Ser Lys Ser Lys Ile Leu Lys Glu Ala
        35                  40                  45

Lys Lys Leu Asn Lys Ala Gln Ala Pro Lys
    50                  55

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 4
cgaattctca tatggcacag cacgacgaag ctgataac                                38

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 5
ctggatccgc cggggcctgt gcgtcgttca g                                       31

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 6
cgaattcagg ccccgcgcgc agataacgca ttt                                33

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 7 ctggatccctt atttcggtgc ctgggctttg tt                                32

<210> SEQ ID NO 8
<211> LENGTH: 58
<212> TYPE: PRT
<213> ORGANISM: Staphylococcus aureus
<220> FEATURE:
<223> OTHER INFORMATION: Protein A mutated immunoglobulin-binding
      domain(PN-23f)

<400> SEQUENCE: 8

Ala Asp Asn Lys Phe Asn Lys Glu Gln Gln Asn Ala Phe Tyr Glu Ile
                 5                  10                  15

Leu His Leu Pro Asn Leu Thr Glu Glu Gln Arg Asn Ala Phe Ile Gln
             20                  25                  30

Ser Leu Arg Asp Asp Pro Ser Val Ser Lys Glu Ile Leu Ala Glu Ala
         35                  40                  45

Lys Lys Leu Asn Asp Ala Gln Ala Pro Lys
     50                  55

<210> SEQ ID NO 9
<211> LENGTH: 58
<212> TYPE: PRT
<213> ORGANISM: Artificial Sequence
<220> FEATURE:
<223> OTHER INFORMATION: modified immunoglobulin-binding protein(PN-28f)

<400> SEQUENCE: 9

Ala Asp Asn Ala Phe Asn Thr Glu Gln Gln Asn Ala Phe Tyr Glu Ile
                 5                  10                  15

Leu His Leu Pro Asn Leu Thr Glu Glu Gln Arg Asn Ala Phe Ile Gln
             20                  25                  30

Ser Leu Arg Asp Asp Pro Ser Lys Ser Lys Lys Ile Leu Lys Glu Ala
         35                  40                  45

Lys Lys Leu Asn Lys Lys Gln Lys Pro Lys
     50                  55

<210> SEQ ID NO 10
<211> LENGTH: 58
<212> TYPE: PRT
<213> ORGANISM: Staphylococcus aureus
<220> FEATURE:
<223> OTHER INFORMATION: Protein A mutated immunoglobulin-binding
      domain(PN-61f)

```
<400> SEQUENCE: 10

Ala Asp Asn Ala Phe Asn Thr Glu Gln Gln Asn Ala Phe Tyr Glu Ile
 1               5                  10                  15

Leu His Leu Pro Asn Leu Thr Glu Glu Gln Arg Asn Ala Phe Ile Gln
             20                  25                  30

Ser Leu Arg Asp Asp Pro Ser Val Ser Lys Glu Ile Leu Ala Glu Ala
         35                  40                  45

Lys Lys Leu Asn Asp Ala Gln Ala Pro Lys
         50                  55

<210> SEQ ID NO 11
<211> LENGTH: 58
<212> TYPE: PRT
<213> ORGANISM: Artificial Sequence
<220> FEATURE:
<223> OTHER INFORMATION: modified immunoglobulin-binding protein(PN-83f)

<400> SEQUENCE: 11

Ala Asp Asn Lys Phe Asn Lys Glu Gln Gln Asn Ala Phe Tyr Glu Ile
 1               5                  10                  15

Leu His Leu Pro Asn Leu Thr Glu Glu Gln Arg Asn Ala Phe Ile Gln
             20                  25                  30

Ser Leu Arg Asp Asp Pro Ser Lys Ser Lys Lys Ile Leu Lys Glu Ala
         35                  40                  45

Lys Lys Leu Asn Lys Ala Gln Ala Pro Lys
         50                  55

<210> SEQ ID NO 12
<211> LENGTH: 58
<212> TYPE: PRT
<213> ORGANISM: Staphylococcus aureus
<220> FEATURE:
<223> OTHER INFORMATION: Protein A mutated immunoglobulin-binding
      domain(PN-87f)

<400> SEQUENCE: 12

Ala Asp Asn Ala Phe Asn Lys Glu Gln Gln Asn Ala Phe Tyr Glu Ile
 1               5                  10                  15

Leu His Leu Pro Asn Leu Thr Glu Glu Gln Arg Asn Ala Phe Ile Gln
             20                  25                  30

Ser Leu Arg Asp Asp Pro Ser Val Ser Lys Glu Ile Leu Ala Glu Ala
         35                  40                  45

Lys Lys Leu Asn Asp Ala Gln Ala Pro Lys
         50                  55
```